United States Patent
Shekalim (10) Patent No.: US 6,254,576 B1
(45) Date of Patent: Jul. 3, 2001

(54) PRESSURE-RESPONSIVE FLOW REGULATOR AND DRUG DELIVERY DEVICES EMPLOYING THE SAME

(75) Inventor: Avraham Shekalim, Nesher (IL)

(73) Assignee: Medrip Ltd., Migdal Haemek (IL)

( * ) Notice: Subject to any disclaimer, the term of this patent is extended or adjusted under 35 U.S.C. 154(b) by 0 days.

(21) Appl. No.: 09/443,112

(22) Filed: Nov. 18, 1999

(51) Int. Cl.[7] .................................... A61M 5/00
(52) U.S. Cl. ................ 604/246; 604/247; 604/152; 604/153; 604/251; 137/501; 422/103
(58) Field of Search ................ 604/68–71, 151, 604/152, 140, 141, 143, 246, 247, 249, 248, 118, 251; 137/501, 504; 422/103

(56) References Cited

U.S. PATENT DOCUMENTS

| | | |
|---|---|---|
| 4,043,332 | 8/1977 | Metcalf . |
| 4,299,220 | 11/1981 | Dorman . |
| 4,343,305 | 8/1982 | Bron . |
| 4,925,451 | 5/1990 | Amendolia . |
| 5,101,854 | 4/1992 | Bron . |
| 5,137,522 * | 8/1992 | Bron ............................. 604/247 |
| 5,421,363 | 6/1995 | Bron . |
| 6,004,287 * | 12/1999 | Loomis et al. ..................... 604/68 |
| 6,110,427 * | 8/2000 | Uffenheimer ..................... 422/81 |

* cited by examiner

Primary Examiner—Richard K. Seidel
Assistant Examiner—Jennifer Maynard
(74) Attorney, Agent, or Firm—Mark M. Friedman (57) ABSTRACT

A fluid flow regulator of a type having a variable outlet defined by a spacing between an outlet aperture and a flexible diaphragm, and in which the position of the flexible diaphragm varies as a function of a pressure differential between a sensing chamber on a first side of the diaphragm and an outlet chamber on a second side of the diaphragm. The regulator includes an adjustable flow impedance configuration in the flow path from the sensing chamber to the outlet chamber has a two elements providing opposing cylindrical surfaces in sliding contact. One of the cylindrical surfaces has a groove configured to define a flow-attenuating passageway having a net flow vector substantially parallel to the axis of the cylindrical surfaces. Axial relative movement between the elements causes a variation in an extent of overlap between the cylindrical surfaces, thereby varying an operative length of the flow-attenuating passageway.

10 Claims, 6 Drawing Sheets

PRESSURE-RESPONSIVE FLOW REGULATOR AND DRUG DELIVERY DEVICES EMPLOYING THE SAME

FIELD AND BACKGROUND OF THE INVENTION

The present invention relates to drug delivery systems and, in particular, it concerns a fluid flow regulator for regulating the flow of liquid medications.

In many cases, it is desired to administer a fluid medication continuously at a slow rate over a given time period. The most common technique for doing this is by adding the medication to a relatively large amount of physiologically compatible liquid and delivering the resulting mixture through an infusion.

This approach suffers from a number of disadvantages. Firstly, the amounts of liquids generally used may in certain cases cause medical complications. Secondly, the presence of an infusion greatly limits the mobility of the patient. And thirdly, the rate of delivery of the mixture may be imprecise, depending both upon the ability of the operator to correctly adjust the flow rate and on the liquid level within the infusion bag. The problem of precision may be addressed by use of an electromechanical dosage regulator. This, however, is a relatively expensive solution, and does not address the remaining problems mentioned above.

An alternative approach to slow drug delivery is by absorption through the skin by use of adhesive patches. This approach, however, gives very non-uniform dosage, and can only deliver very small quantities of medication.

In an attempt to achieve more uniform dosages at a wide range of flow rates, flow regulators have been developed based on the use of a pressure-responsive flexible diaphragm. The principle of these regulators may be understood by reference to U.S. Pat. Nos. 4,343,305 and 5,421,363 to Dan Bron which are hereby incorporated by reference. The Bron '305 reference discloses a flow regulator for use in an infusion set. The flow regulator includes a body having a cavity divided into two chambers by a flexible diaphragm. The first of these chambers is a pressure sensing chamber. The other is a valving chamber through which the drug flows, the outlet from that chamber being centrally disposed underlying the diaphragm whereby flexing of the diaphragm in one direction as a result of increased pressure in the other chamber adjusts the size of the flow path through the outlet. A rudimentary flow impedance adjustment between the two chambers is proposed as a means for adjusting the flow rate.

The Bron '363 reference proposes an improved adjustment configuration in which a tubular flow attenuator fits within the neck portion of a housing. The flow attenuator is formed with a pattern of grooves which, together with the opposing surface, define a meander-type labyrinth. The relative positions of an inlet and outlet along the labyrinth may be varied by relative rotation between the flow attenuator and the neck portion, thereby changing the operative length of the labyrinth and the consequent flow rate.

The diaphragm-based regulators of Bron provide significant advantages over the slow-dosing techniques described above. Specifically, these regulators provide generally uniform dosing of medication at low flow rates, thereby avoiding the need for the excessive dilution of conventional infusions. The pressure-responsive nature of the regulation also ensures that supply pressure variations are properly compensated. Nevertheless, these regulators suffer from a number of serious shortcomings. Most notably, the full range of adjustment, even for the improved configuration of the '363 patent, corresponds to a range of rotation significantly less than a full revolution. As a result, the regulator is either implemented so as to be limited to a fairly narrow range of flow rates or is overly sensitive to angular displacements offering a low degree of precision in selecting the flow rate.

A further shortcoming of the aforementioned Bron regulators is the complexity of manufacturing high-precision meandering labyrinth grooves around the internal surface of a cylindrical element.

U.S. Pat. No. 5,101,854 also to Bron discloses an alternative design of diaphragm-based flow regulator which employs a flow-attenuating passageway formed by opposing surfaces one of which has a helical groove. The use of a helical groove provides considerable advantages of ease of production and precision. However, no provision is offered for rendering such a helical flow-attenuating passageway adjustable. Instead, adjustment is achieved by changing the outlet geometry directly by raising or lowering the outlet aperture relative to the diaphragm.

Finally, it should be noted that all of the above-mentioned regulators must be connected at all times to an external supply of medication, rendering the drug delivery system a minimum of at least two separate parts and somewhat bulky.

There is therefore a need for a simple diaphragm-based flow regulator, suitable for use in medical applications, which would provide precise control of the flow rate over a wide range of rates. It would also be advantageous to provide a compact drug delivery device which would provide pressure-responsive regulation of drug release from a contained volume.

SUMMARY OF THE INVENTION

The present invention is a continuously-adjustable, pressure-responsive flow regulator. The present invention also provides drug delivery devices employing a flow regulator of this type.

According to the teachings of the present invention, in a fluid flow regulator of a type having a variable outlet defined by a spacing between an outlet aperture and a flexible diaphragm, and in which the position of the flexible diaphragm varies as a function of a pressure differential between a sensing chamber on a first side of the diaphragm and an outlet chamber on a second side of the diaphragm, there is provided an adjustable flow impedance configuration disposed in a flow path passing from a first point in substantially direct fluid communication with the sensing chamber to the outlet chamber, the adjustable flow impedance configuration comprising: (a) a first element providing a first substantially cylindrical outer surface, reference being made to a central axis of the first cylindrical surface; and (b) a second element providing a second substantially cylindrical inner surface deployed coaxially, and in sliding contact, with the first surface, wherein at least one of the first and second cylindrical surfaces features at least one groove configured to define a flow-attenuating passageway between the first and second cylindrical surfaces, the flow-attenuating passageway having a net flow vector substantially parallel to the axis, the first and second elements being configured such that axial movement of the first element relative to the second element causes a variation in an extent of overlap between the first and second cylindrical surfaces, thereby varying an operative length of the flow-attenuating passageway.

According to a further feature of the present invention, the at least one groove is a helical groove.

According to a further feature of the present invention, the first element features a first threaded adjustment portion and the second element features a complementary threaded adjustment portion deployed in engagement with the first threaded adjustment portion such that rotation of the first element relative to the second element about the axis generates movement of the first component relative to the second component along the axis.

According to a further feature of the present invention, the operative length of the flow-attenuating passageway varies in a substantially continuous manner with rotation of the first element relative to the second element about the axis over a range of a plurality of revolutions of the relative rotation.

According to a further feature of the present invention, the at least one groove has at least a first portion configured to produce a flow-attenuating passageway having a first cross-sectional area and a second portion configured to produce a flow-attenuating passageway having a second cross-sectional area greater than the first cross-sectional area.

There is also provided according to the teachings of the present invention, a constant flow fluid delivery device comprising: (a) at least one body component defining a cavity; (b) a flexible diaphragm deployed within the cavity so as to divide the cavity into a storage chamber and an outlet-side chamber; (c) at least one flow-path-defining component associated with the body so as to define a flow path from a first point in substantially direct fluid communication with the storage chamber passing via a fluid flow restriction to the outlet-side chamber, the fluid flow restriction being formed as a flow-attenuating passageway lying substantially on a virtual cylinder; (d) an outlet from the outlet-side chamber, the outlet being configured such that flexing of the diaphragm in a given direction in response to increased pressure in the storage chamber restricts flow through the outlet; and (e) a pressure applicator deployed within the storage chamber so as to apply above-atmospheric pressure to a fluid within the storage chamber, wherein at least part of the storage chamber lies concentrically within the virtual cylinder of the flow-attenuating passageway.

According to a further feature of the present invention, the pressure applicator includes a spring-loaded piston. Preferably, the spring-loaded piston is configured to be manually retractable to facilitate filling of the storage chamber.

According to a further feature of the present invention, the pressure applicator includes an inflatable balloon.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a continuously-adjustable, pressure-responsive flow regulator. The present invention also provides drug delivery devices employing a flow regulator of this type.

The principles and operation of flow regulators and drug delivery devices according to the present invention may be better understood with reference to the drawings and the accompanying description.

Figure 1:
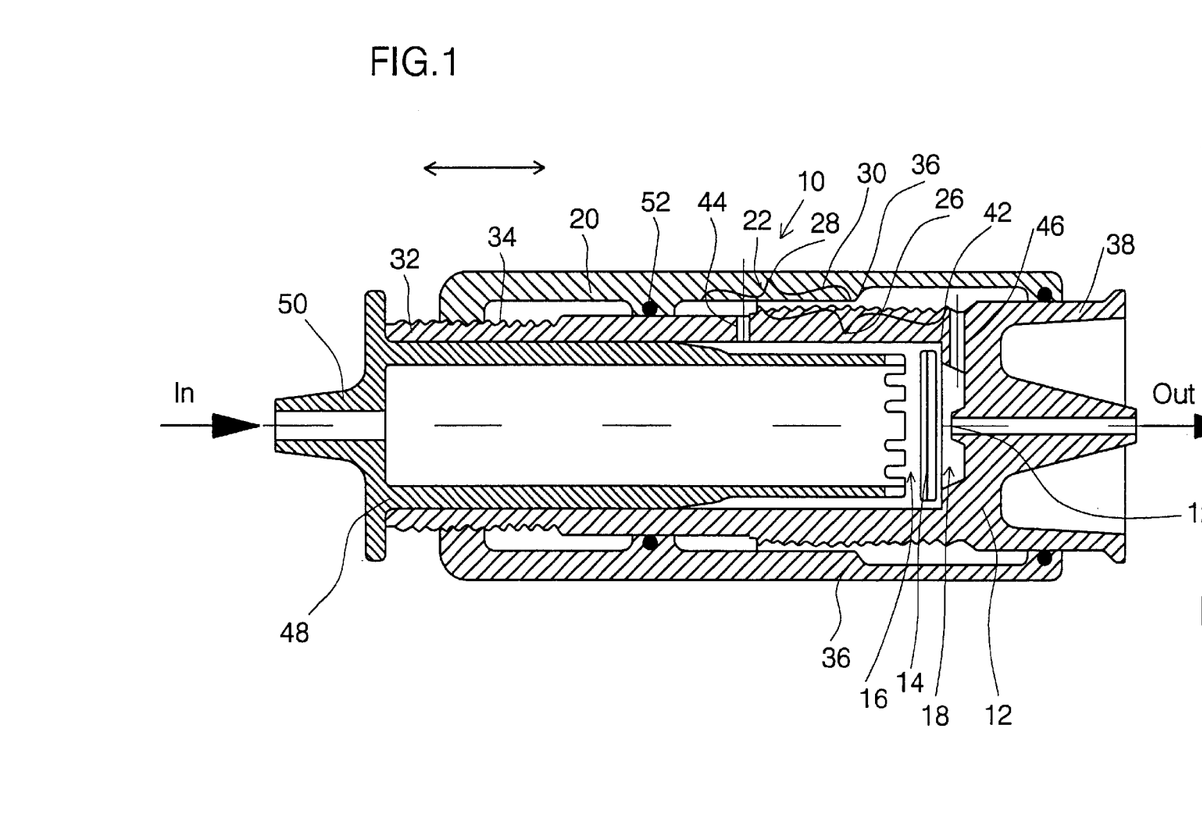
FIG. 1 is a cross-sectional view taken through a continuously-adjustable, pressure-responsive flow regulator, constructed and operative according to the teachings of the present invention.

Referring now to the drawings, FIG. 1 shows a continuously-adjustable, pressure-responsive fluid flow regulator, generally designated 10, constructed and operative according to the teachings of the present invention.

The principle of operation of flow regulator 10 is essentially similar to that of the aforementioned diaphragm-based regulators known in the art. Thus, in flow regulator 10 includes at least one body component 12 defining a cavity, and a flexible diaphragm 14 deployed within the cavity so as to divide the cavity into an inlet-side chamber 16 and an outlet-side chamber 18. At least one flow-path-defining component 20 is associated with body component 12 so as to define a flow path from a first point in substantially direct fluid communication with inlet-side chamber 16 passing via a fluid flow restriction 22 to outlet-side chamber 18. An outlet 24 from outlet-side chamber 18 is configured such that flexing of diaphragm 14 in a given direction in response to increased pressure in inlet-side chamber 16 restricts flow through outlet 24.

It is a particular feature of most preferred implementations of the present invention that fluid flow restriction 22 is formed as an adjustable flow-attenuating passageway at the interface between flow-path-defining component 20 and body component 12 in such a manner that its operative length may be changed by axial displacement of flow-path-defining component 20 relative to body component 12.

Thus, in the example shown, body component 12 provides a first substantially cylindrical outer surface 26, and flow-path-defining component 20 provides a second substantially cylindrical inner surface 28 deployed coaxially, and in sliding contact, with first cylindrical surface 26. At least one of first and second cylindrical surfaces 26 and 28 features at least one groove 30 configured to define a flow-attenuating passageway between surfaces 26 and 28. This flow-attenuating passageway is configured to have a net flow vector substantially parallel to the axis of the cylindrical surfaces. Flow-path-defining component 20 and body component 12 are further configured such that relative axial movement between them causes a variation in an extent of overlap between the first and second cylindrical surfaces 26 and 28, thereby varying the operative length of the flow-attenuating passageway.

The flow-attenuating passageway is described as having a net flow vector substantially parallel to the axis of the cylindrical surfaces. The term flow-attenuating passageway as used in the field of fluid flow regulation refers to a structure which produces an artificially elongated flow path between two points. This may be achieved by introducing a meandering flow path (labyrinth) between the two end points or alternatively, in the case of a cylindrical passageway, by producing an elongated helical flow path. In either case, the term "net flow vector" is used herein to denote the net path followed by the fluid from its inlet into the passageway to its outlet therefrom neglecting the "detours" taken within the passageway itself.

In the present case, this net flow vector is described as "substantially parallel" to the axis of the cylindrical surfaces to the extent that the length of the passageway traveled is a direct, typically linear, function of the axial distance traveled along the cylinder. It should be noted that the net flow path may not be truly parallel to the axis since the angular disposition of the inlet and outlet about the axis need not be the same and typically varies during adjustment, as will become clear below.

Groove 30 may be formed on either of first and second cylindrical surfaces 26 and 28, i.e., as part of either body component 12 or flow-path-defining component 20. Thus, the invention will be described herein with reference to FIGS. 1–7 employing an example in which groove 30 is formed on surface 26 as part of body component 12. FIGS. 8A and 8B show an equivalent regulator 10', constructed and operative according to the teachings of the present invention, employing the reverse configuration.

As mentioned above, the "operative length" of the flow-attenuating passageway is a function of the extent of overlap between the first and second cylindrical surfaces 26 and 28. Specifically, in the case shown here that groove 30 is formed on surface 26, surface 28 is delimited by a recess 36 which is preferably formed as a general widening of the internal diameter of flow-path-defining component 20 as shown. Thus, the length over which the fluid flow is limited to the flow-attenuating passageway is set by the degree of over-lapping contact between surfaces 26 and 28, starting from the left-hand end of groove 30 as shown and terminating at recess 36. This length is referred to as the "operative length" of the flow-attenuating passageway.

Turning now to the details of flow regulator 10 in more detail, in a particularly preferred implementation of the present invention, groove 30 is formed as a helical groove. This has advantages for the ease of manufacture and level of precision with which the groove can be produced. Optionally, more than one groove 30 can be deployed in a double- or triple-helix, although a single helix is generally preferred.

In order to facilitate precise adjustment of the relative axial positions of body component 12 and flow-path-defining component 20, these are preferably provided with complementary threaded adjustment portions 32 and 34, respectively. These threaded adjustment portions are deployed in engagement with each other such that rotation of flow-path-defining component 20 relative to body component 12 about the central axis generates slow and accurately-controllable relative movement between them in an axial direction. The pitch of the threaded portions is preferably chosen such that the full range of adjustment of the operative length of the flow-attenuating passageway corresponds to at least two, preferably at least three, and most preferably no less than five, complete turns of flow-path-defining component 20 relative to body component 12 about the central axis. This facilitates precise adjustment of the flow rate across substantially the full range of flow rates accommodated by flow regulator 10.

It should be noted that the present invention is applicable to applications over a wide range of flow rates. Thus, at one extreme, the device may be used for infusion rates of up to about 10 liters per hour. At the other extreme, it may be used to advantage such as in the dispensing device applications of the present invention described below for dispensing rates in the range of milliliters per hour or even tenths of milliliters. Where designed specifically for a given set of applications requiring only a given sub-range of the flow rates mentioned, the size of groove 30 may be chosen to provide maximum sensitivity over the intended sub-range. According to one particularly preferred option, flow regulator 10 is implemented with the capability of multiple-stage graduated sensitivity adjustment as will now be described with reference to FIG. 8B.

Specifically, according to the preferred option illustrated in FIG. 8B, groove 30 is formed with a variable cross-sectional area in such a manner as to provide sensitivity of adjustment appropriate to the flow rate setting. In the example shown, the groove is subdivided into three portions. The first portion to come into overlapping relation, designated 30a, has a relatively large cross-sectional area to provide flow rate adjustment suited to higher flow rates. The middle portion, designated 30b, has a smaller area suited to finer adjustments. The third portion, designated 30c, which only comes into overlapping relation at the lowest flow rates, has a small cross-sectional area to provide the required sensitivity of adjustment at such low rates. By way of example, flow regulator 10 may be configured such that the three ranges correspond respectively to flow rates from 10 liters/hour (l/hr) down to 1 l/hr, from 1 l/hr down to 10 ml/hr, and from 10 ml/hr down to 100 µl/hr.

Clearly, the subdivision of groove 30 into three portions in the manner described is only one example of the use of a variable groove size. In an alternative preferred implementation (not shown), the groove size varies in a continuous, or near continuous, manner to provide what approximates to a logarithmic scale adjustment. In a further preferred alternative (not shown), the groove size may be varied in a continuous, or near continuous, manner in the reverse direction, i.e., such that the smaller cross-section is first to come into overlapping relation with the opposing surface. This latter option may be used to provide linear, or near-linear, variation of the flow rate with the number of turns through which the adjustment mechanism is turned.

At least one scale 38 is typically provided to indicate the flow rate to which the regulator is set. In a preferred implementation, scale 38 is deployed to provide an indication based on axial displacement between body component 12 and flow-path-defining component 20. Adjustment along this scale by use of multiple turns offers much higher resolutions than could reliably be achieved using the single-revolution adjustment proposed by the aforementioned U.S. Pat. No. 5,421,363.

To complete the structural description of regulator 10, it will be noted that body component 12 preferably also serves to define a seat 42 defining the position of the periphery of diaphragm 14, at least one radial passage 44 from inlet-side chamber 16 to flow restriction 22, at least one radial passage 46 from flow restriction 22 to outlet-side chamber 18, and the outlet aperture 24. For conventional in-line flow regulation applications, such as the infusion regulation application shown schematically in FIG. 2, an adapter element 48 is added to provide the inlet connection 50 of regulator 10. Adapter element 48 also retains diaphragm 14 to prevent it becoming removed from seat 42 in the event of a reverse flow (cases of which will be mentioned below), but is configured to ensure an unobstructed flow path to passageway 44.

Figure 2:
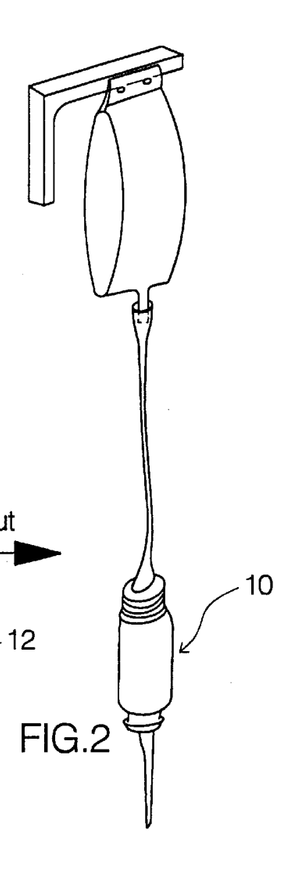
FIG. 2 is a schematic representation of an application of the flow regulator of FIG. 1 in an infusion line.

In use, flow regulator 10 is connected in line, for example as shown in FIG. 2, and is adjusted by rotation of flow-path-defining component 20 to the required flow rate setting. Preferably, flow-path-defining component 20 is configured so provide one or both of a fully closed and a fully open extreme state. The fully closed state may conveniently be provided by forming flow-path-defining component 20 such that one of its seals 52 overlies and obstructs passageway 44 in the extreme low-flow position. The filly open "short-circuit" state may conveniently be provided by ensuring that recess 36 moves beyond the start of groove 30 in the extreme high-flow position.

Turning now to FIGS. 3–7, according to further embodiments of the present invention, the regulator structure described thus far forms the basis of highly-compact, self-contained, constant-flow fluid delivery devices which may be used as a replacement for slow-dosing arrangements such as syringe pumps. Specifically, the hollow, coaxial, cylindrical form of both body component 12 and flow-path-defining component 20 provides a hollow core which serves as a storage chamber disposed concentrically at least partially within the virtual cylinder of the flow-attenuating passageway. The fluid delivery devices are completed by a pressure applicator deployed within this storage chamber (replacing adapter 48 of FIG. 1) so as to apply above-atmospheric pressure to a fluid within the storage chamber, thereby dispensing the fluid.

Figures 3, 4:
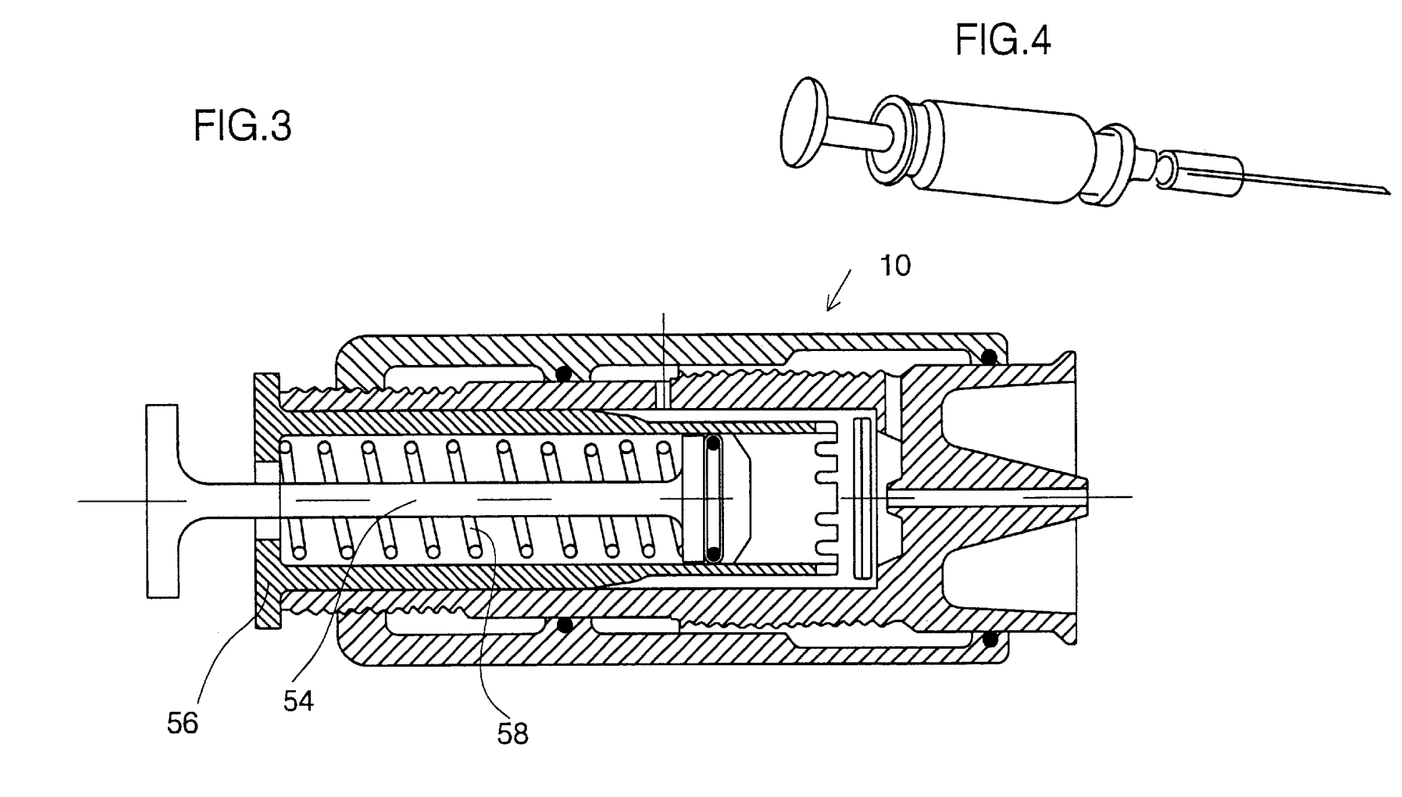
FIG. 3 is a cross-sectional view taken through a first embodiment of a drug delivery device, constructed and operative according to the teachings of the present invention, including the flow regulator of FIG. 1.
FIG. 4 is a schematic representation of an application of the drug delivery device of FIG. 3 as a slow-release syringe.

In a first example shown in FIGS. 3 and 4, the pressure applicator is employs a spring-loaded piston 54 which is urged forward in relation to an insert sleeve 56 by a helical spring 58. The external and front end surfaces of insert sleeve 56 are similar to the corresponding surfaces of adapter 48 described above. In this case, piston 54 extends from the rear of insert sleeve 56 so as to be manually retractable. This allows manual filling of the storage chamber by retraction of the piston while the front of the dispenser is immersed in the fluid. Optionally, this and other examples of the dispenser may be configured so that diaphragm 14 becomes lifted slightly from seat 42 by the reverse pressure during filling, thereby allowing the fluid flow to bypass flow restriction 22. FIG. 4 shows a typical application of this dispenser, directly connected to a needle.

Figure 5:
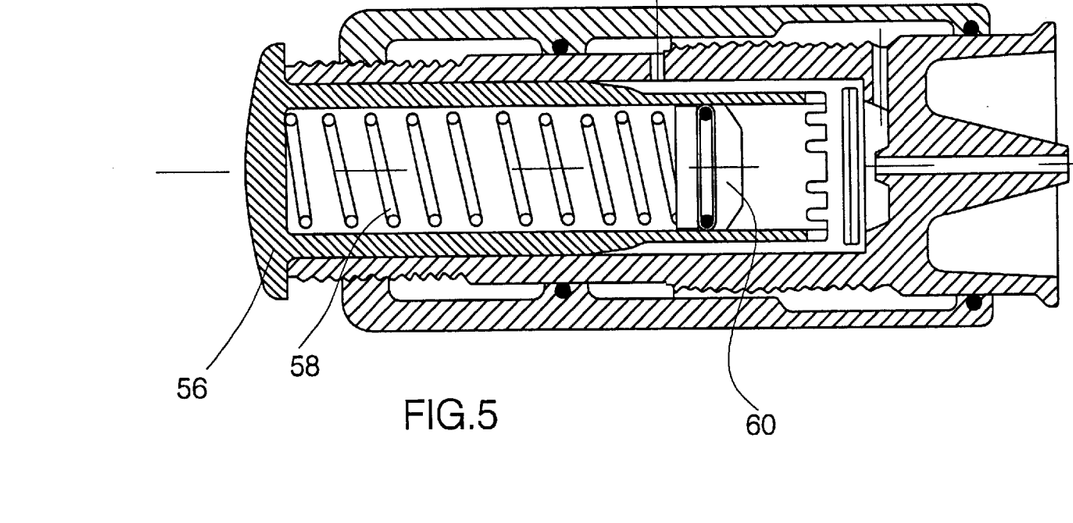
FIG. 5 is a cross-sectional view taken through a second embodiment of a drug delivery device, constructed and operative according to the teachings of the present invention, including the flow regulator of FIG. 1.
Figure 6A:
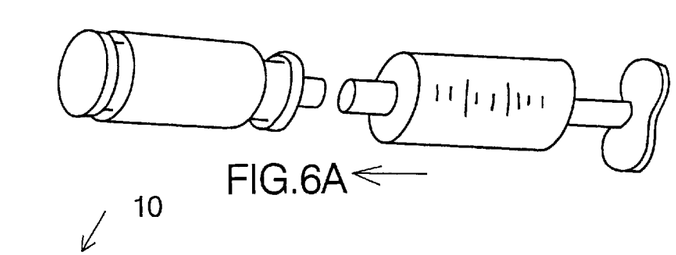
FIGS. 6A and 6B are schematic representations of an application of the drug delivery device of FIG. 5 showing it, respectively, during filling and in use as a slow-release syringe.
Figure 6B:
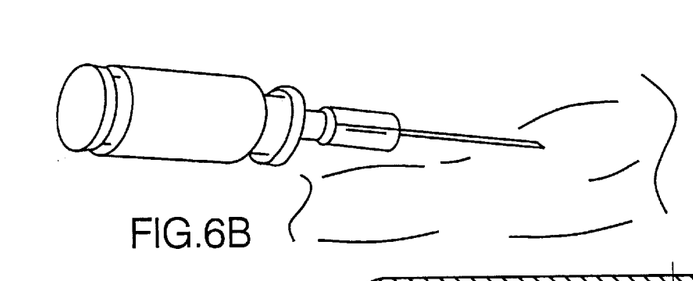

FIGS. 5, 6A and 6B show a fluid dispenser similar to that of FIGS. 3 and 4 in which the spring-loaded piston 60 is implemented as a closed unit not manually retractable. In this case, filling must be done by application of back pressure, such as with a syringe (FIG. 6A). Once full, the syringe is removed and the dispenser may be sealed and stored until required for use. A needle may then be attached (FIG. 6B) for use in the same manner as the previous embodiment.

Figure 7:
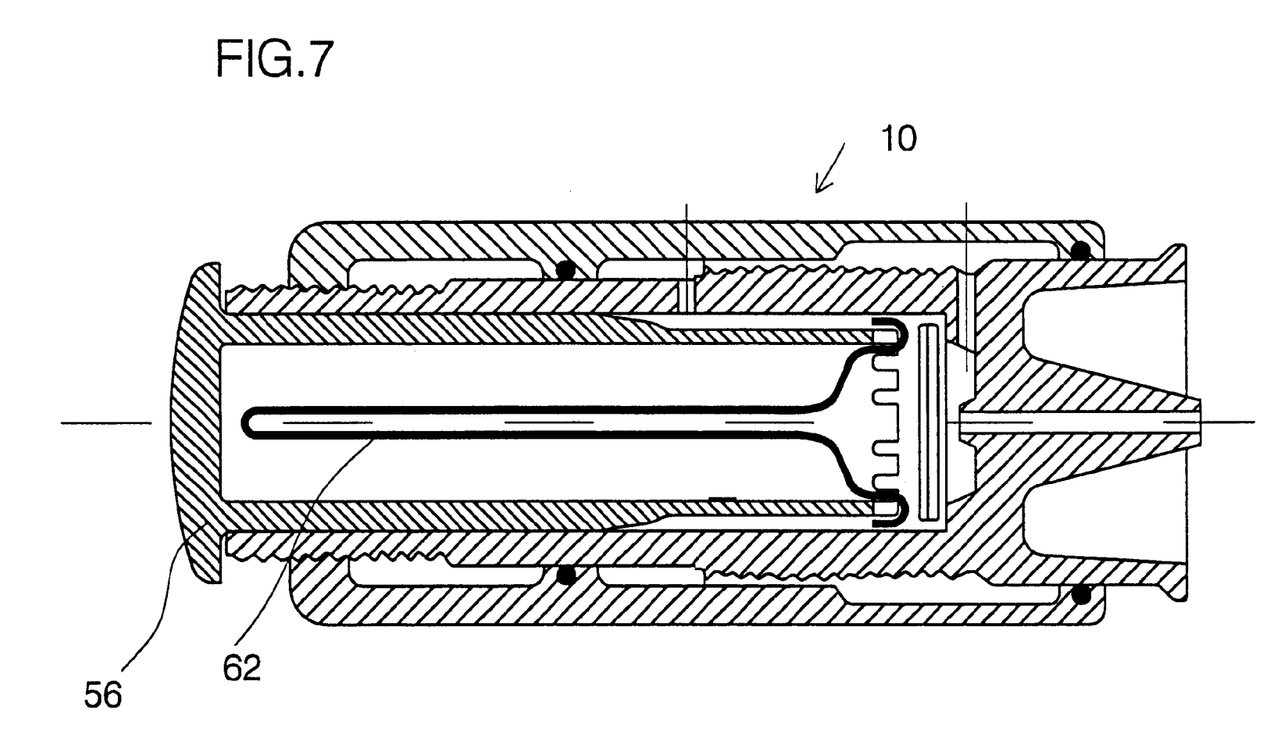
FIG. 7 is a cross-sectional view taken through a variant of the drug delivery device of FIG. 5.
Figure 8A:
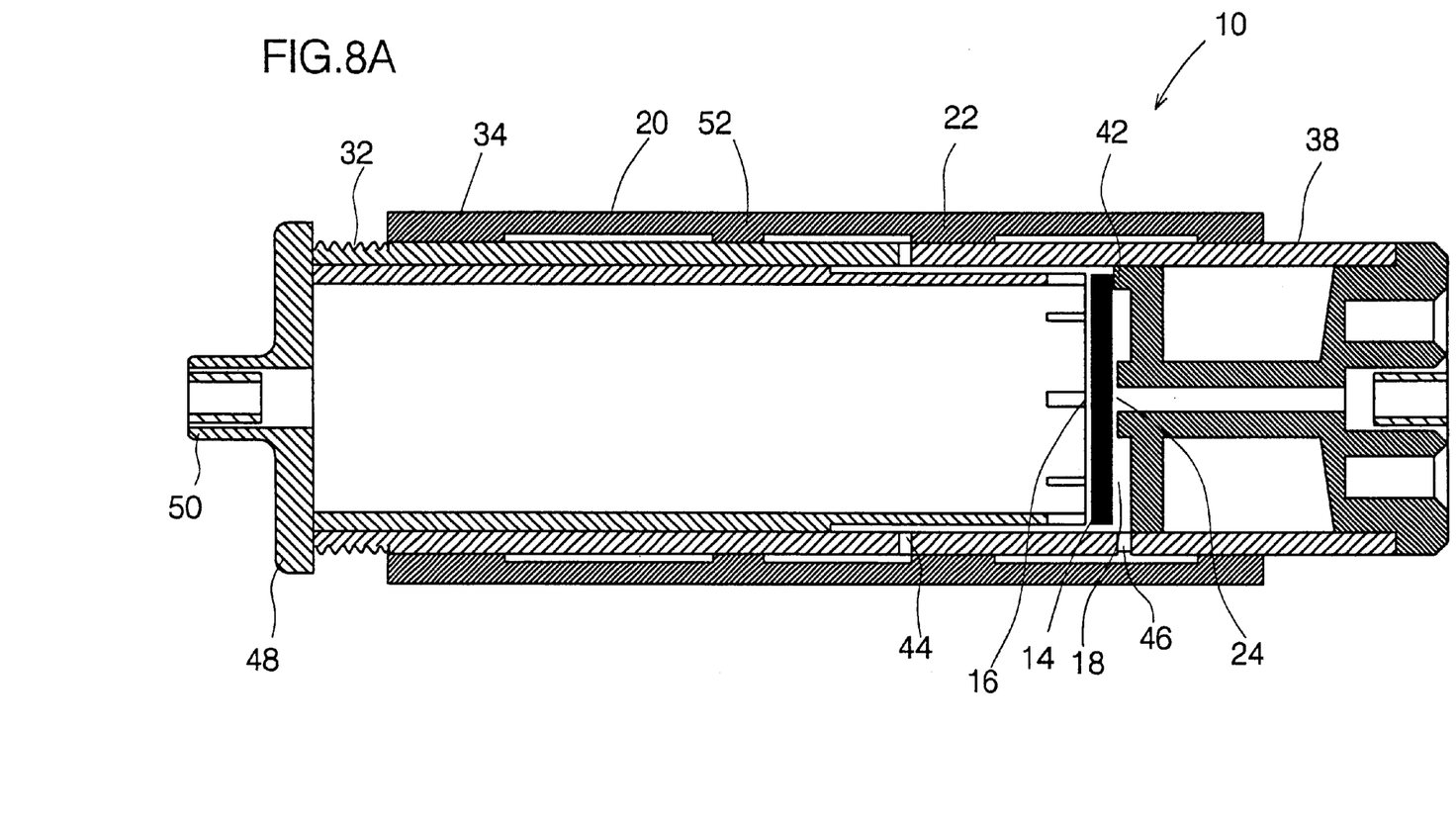
FIG. 8A is a cross-sectional view taken through a continuously-adjustable, pressure-responsive flow regulator equivalent to that of FIG. 1 but showing a reversed configuration.
Figure 8B:
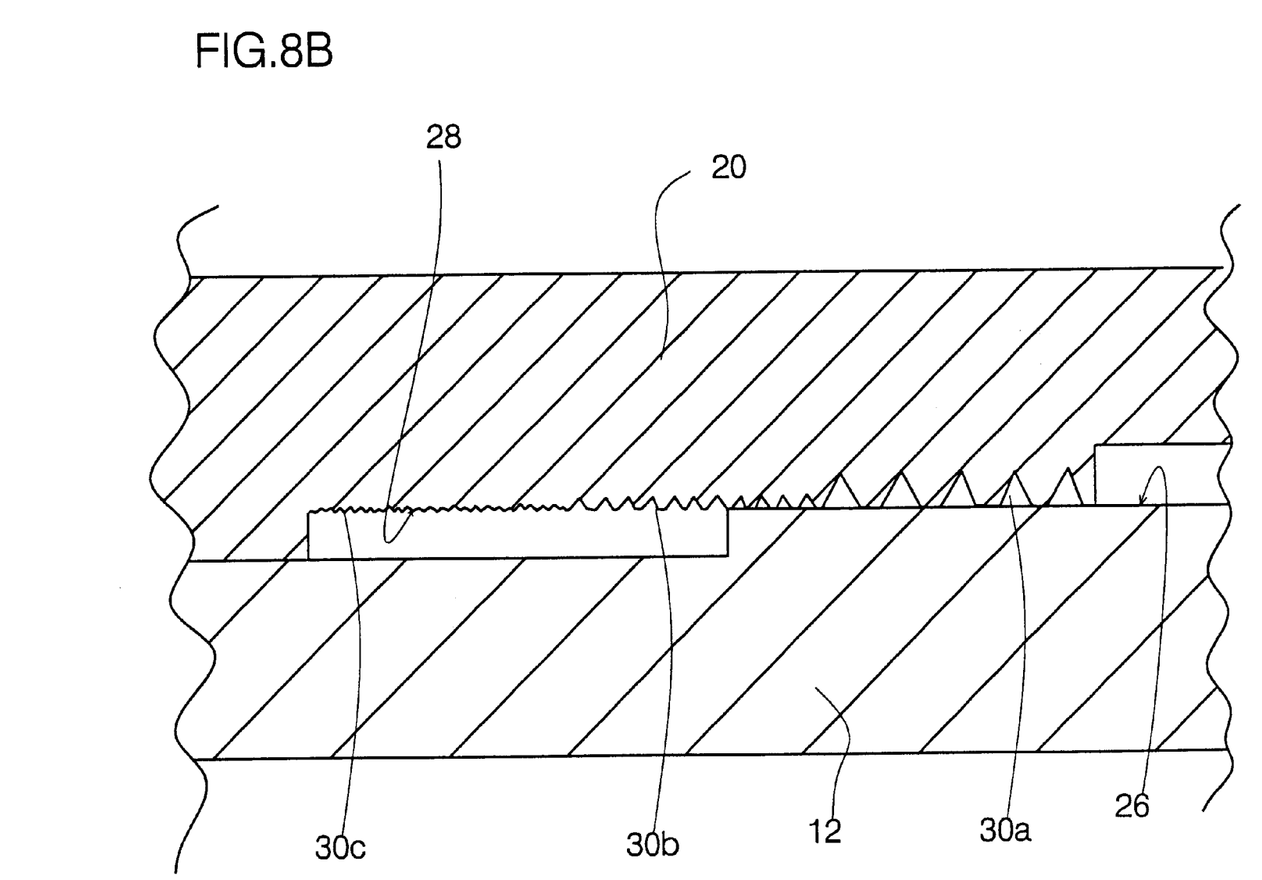
FIG. 8B is a partial enlarged view of the flow regulator of FIG. 8A showing a graduated sensitivity adjustment option.

Finally, turning to FIG. 7, there is shown an additional embodiment of a fluid dispenser, functionally identical to that of FIG. 5. In this case, the pressure applicator is implemented using an inflatable balloon 62. Balloon 62 may be made from a range of medical grade materials including, but not limited to, silicone rubber, latex and stainless steel.

In all other respects, the structure and operation of the dispensing devices of FIGS. 3–7 are fully analogous to, and will be understood by reference to, those of regulator 10 described above in detail with reference to FIGS. 1 and 2.

It will be appreciated that the above descriptions are intended only to serve as examples, and that many other embodiments are possible within the spirit and the scope of the present invention.

What is claimed is:

1. A fluid flow regulator comprising a variable outlet defined by a spacing between an outlet aperture and a flexible diaphragm, and in which the position of the flexible diaphragm varies as a function of a pressure differential between a sensing chamber on a first side of the diaphragm and an outlet chamber on a second side of the diaphragm, an adjustable flow impedance configuration being disposed in a flow path passing from a first point in substantially direct fluid communication with said sensing chamber to said outlet chamber, the ajustable flow impedance configuration including:

(a) a first element providing a first substantially cylindrical outer surface, said first cylindrical surface defining a central axis; and (b) a second element providing a second substantially cylindrical inner surface deployed coaxially, and in sliding contact, with said first surface, wherein at lease one of said first and second cylindrical surfaces features at least one groove configured to define a flow-attenuating passageway between said first and second cylindrical surfaces, said flow-attenuating passageway having a net flow vector substantially parallel to said axis, said first and second elements being configured such that axial movement of said first element relative to said second element causes a variation in an extent of overlap between said first and second cylindrical surfaces, thereby varying an operative length of said flow-attenuating passageway.

2. The adjustable flow impedance configuration of claim 1, wherein said at least one groove is a helical groove.

3. The adjustable flow impedance configuration of claim 1, wherein said first element features a first threaded adjustment portion and said second element features a complementary threaded adjustment portion deployed in engagement with said first threaded adjustment potion such that rotation of said first element relative to said element about said axis generates movement of said first element relative to said second element along said axis.

4. The adjustable flow impedance configuration of claim 3, wherein said operative length of said flow-attenuating passageway varies in a substantially continuous manner with rotation of said first element relative to said second element about said axis over a range of a plurality of revolutions of said relative rotation.

5. The adjustable flow impedance configuration of claim 1, wherein said at least one groove has at least a first portion configured to produce a flow-attenuating passageway having a first cross-sectional area and a second portion configured to produce a flow-attenuating passageway having a second cross-sectional area greater than said first cross-sectional area.

6. A constant flow fluid delivery device comprising:

(a) at least one body component defining a cavity;

(b) a flexible diaphragm deployed within said cavity so as to divide said cavity into a storage chamber and an outlet-side chamber;

(c) at least one flow-path-defining component associated with said body so as to define a flow path from a first point in substantially direct fluid communication with said storage chamber passing via a fluid flow restriction to said outlet-side chamber, said fluid flow restriction being formed as a flow-attenuating passageway lying substantially on a virtual cylinder;

(d) an outlet from said outlet-side chamber, said outlet being configured such that flexing of said diaphragm in a given direction in response to increased pressure in said storage chamber restricts flow through said outlet; and (e) a pressure applicator deployed within said storage chamber so as to apply above-atmospheric pressure to a fluid within said storage chamber, wherein at least part of said storage chamber lies concentrically within the virtual cylinder of said flow-attenuating passageway.

7. The fluid delivery device of claim 6, wherein said at least one flow-path-defining component is configured such that a flow impedance of said fluid flow restriction is adjustable by axial movement of said at least one flow-path-defining component relative to said body component.

8. The fluid delivery device of claim 6, wherein said pressure applicator includes a spring-loaded piston.

9. The fluid delivery device of claim 8, wherein said spring-loaded piston is configured to be manually retractable to facilitate filling of said storage chamber.

10. The fluid delivery device of claim 6, wherein said pressure applicator includes an inflatable balloon.

* * * * *